US012228534B2

United States Patent
Li et al.

(10) Patent No.: US 12,228,534 B2
(45) Date of Patent: Feb. 18, 2025

(54) CAPACITIVE SENSOR FOR MONITORING GAS CONCENTRATION

(71) Applicant: Applied Materials, Inc., Santa Clara, CA (US)

(72) Inventors: Xiaopu Li, San Jose, CA (US); Kallol Bera, San Jose, CA (US); Yaoling Pan, San Jose, CA (US); Kelvin Chan, San Ramon, CA (US); Amir Bayati, San Jose, CA (US); Philip Allan Kraus, San Jose, CA (US); Kenric T. Choi, San Jose, CA (US); William John Durand, San Francisco, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 18/604,257

(22) Filed: Mar. 13, 2024

(65) Prior Publication Data
US 2024/0219337 A1    Jul. 4, 2024

Related U.S. Application Data

(62) Division of application No. 17/166,967, filed on Feb. 3, 2021, now Pat. No. 11,959,868.

(51) Int. Cl.
*C23C 16/40*    (2006.01)
*C23C 16/455*    (2006.01)
(Continued)

(52) U.S. Cl.
CPC ....... *G01N 27/22* (2013.01); *C23C 16/45544* (2013.01); *C23C 16/45561* (2013.01);
(Continued)

(58) Field of Classification Search
CPC ........... G01N 27/4071; G01N 27/4067; G01N 27/4077; G01N 27/227; G01N 2027/222; G01N 27/226; G01N 27/4141; G01N 15/0656; G01N 27/026; G01N 27/221; G01N 27/02; G01N 27/22; G01N 27/4075; G01N 27/404; G01N 27/4162; G01N 21/783; G01N 2291/02809;
(Continued)

(56) References Cited

U.S. PATENT DOCUMENTS 7,485,189 B2    2/2009  Satake et al.
2018/0067003 A1* 3/2018  Michiwaki ............ G01L 5/0004
(Continued)

OTHER PUBLICATIONS

Non-Final Office Action from U.S. Appl. No. 17/166,967 dated Apr. 5, 2023, 11 pgs.
(Continued)

*Primary Examiner* — Rudy Zervigon
(74) *Attorney, Agent, or Firm* — Schwabe, Williamson & Wyatt, P.C.

(57) ABSTRACT

Embodiments disclosed herein include gas concentration sensors, and methods of using such gas concentration sensors. In an embodiment, a gas concentration sensor comprises a first electrode. In an embodiment the first electrode comprises first fingers. In an embodiment, the gas concentration sensor further comprises a second electrode. In an embodiment, the second electrode comprises second fingers that are interdigitated with the first fingers.

19 Claims, 10 Drawing Sheets

(51) Int. Cl.
  *C23C 16/52*    (2006.01)
  *G01N 27/22*    (2006.01)
  *G01N 33/00*    (2006.01)
  *H01L 21/67*    (2006.01)

(52) U.S. Cl.
  CPC ......... *C23C 16/52* (2013.01); *G01N 33/0027* (2013.01); *H01L 21/67017* (2013.01); *H01L 21/67253* (2013.01)

(58) Field of Classification Search
  CPC .......... G01N 2291/02872; G01N 2291/02881; G01N 27/407; G01N 2291/021; G01N 33/0027; C23C 16/45544; C23C 16/45561; C23C 16/52; H01L 21/67017; H01L 21/67253
  USPC ...................................... 118/663; 156/345.24
  See application file for complete search history.

(56) References Cited

U.S. PATENT DOCUMENTS

2020/0116663 A1*   4/2020   Tuncer .................... H01L 24/11
2022/0381730 A1*   12/2022   Childress ........... G01N 33/0021

OTHER PUBLICATIONS

Final Office Action from U.S. Appl. No. 17/166,967 dated Aug. 8, 2023, 13 pgs.

\* cited by examiner

CAPACITIVE SENSOR FOR MONITORING GAS CONCENTRATION

CROSS-REFERENCE TO RELATED APPLICATIONS

This application is a divisional of U.S. patent application Ser. No. 17/166,967, filed on Feb. 3, 2021, the entire contents of which are hereby incorporated by reference herein.

BACKGROUND

1) Field

Embodiments of the present disclosure pertain to the field of semiconductor processing and, in particular, to capacitive gas concentration sensors.

2) Description of Related Art

As semiconductor manufacturing continues to scale to smaller and smaller critical dimension (CD) and feature sizes, it becomes more important to precisely control chamber processing conditions. One such chamber condition is the concentration of gasses that are flown into the chamber. Currently, mass flow meters and valves are used to set the flow of gasses into the chamber. However, such devices do not provide the necessary resolution for advanced nanoscale device high volume manufacturing process. The direct monitor and control of the gas concentrations is critical and necessary.

In some instances laser sensors have been used to provide more accurate control of gas concentration into chambers. Laser sensors have been used in research settings. However, laser sensors are complicated and difficult to integrate into the processing tool. As such, laser sensors are not cost effective, and are exceedingly difficult to integrate into tools used for high volume manufacturing (HVM) environments.

SUMMARY

Embodiments disclosed herein include gas concentration sensors, and methods of using such gas concentration sensors. In an embodiment, a gas concentration sensor comprises a first electrode. In an embodiment the first electrode comprises first fingers. In an embodiment, the gas concentration sensor further comprises a second electrode. In an embodiment, the second electrode comprises second fingers that are interdigitated with the first fingers.

Embodiments disclosed herein may also comprise a semiconductor processing tool. In an embodiment, the semiconductor processing tool comprises a chamber, a gas line for providing a source gas to the chamber, and a gas concentration sensor in the gas line. In an embodiment, the gas concentration sensor comprises a first electrode, where the first electrode comprises first fingers. In an embodiment, the gas concentration sensor further comprises a second electrode, where the second electrode comprises second fingers that are interdigitated with the first fingers.

Embodiments disclosed herein may also comprise a gas feed architecture that comprises a first gas line, where the first gas line receives a first gas from a first gas source. In an embodiment an ampule is along the first gas line, and the ampule supplies a second gas to the first gas line. In an embodiment, a first gas concentration sensor is after the ampule. In an embodiment, the first gas concentration sensor comprises a first electrode, where the first electrode comprises first fingers, and a second electrode, where the second electrode comprises second fingers that are interdigitated with the first fingers.

DETAILED DESCRIPTION

Capacitive gas concentration sensors are described herein. In the following description, numerous specific details are set forth in order to provide a thorough understanding of embodiments of the present disclosure. It will be apparent to one skilled in the art that embodiments of the present disclosure may be practiced without these specific details. In other instances, well-known aspects, such as integrated circuit fabrication, sensor fabrication, sensor module packaging/integration, are not described in detail in order to not unnecessarily obscure embodiments of the present disclosure. Furthermore, it is to be understood that the various embodiments shown in the Figures are illustrative representations and are not necessarily drawn to scale.

As noted above, advanced semiconductor processing requires precise control of processing parameters, such as gas concentrations in gasses flown into the processing chamber. In order to allow for precise (e.g, the resolution can be as low as a few ppm) gas concentration measurements in high volume manufacturing environments, the gas concentration sensor needs to be simple, low cost, and easily integrated into the processing environment.

Accordingly, embodiments disclosed herein include capacitive sensor architectures for determining gas concentrations. In an embodiment, the capacitive sensors are easily integrated into the gas lines of semiconductor processing tools. Furthermore, embodiments disclosed herein include capacitive sensor architectures that are able to detect parts per million (PPM) concentrations. Accordingly, incredibly high precision of the gas concentrations flown into the chamber can be obtained. Additionally, through integration of multiple capacitive sensors and gas feed architectures, even greater precision of the gas concentrations can be obtained.

Figure 1:
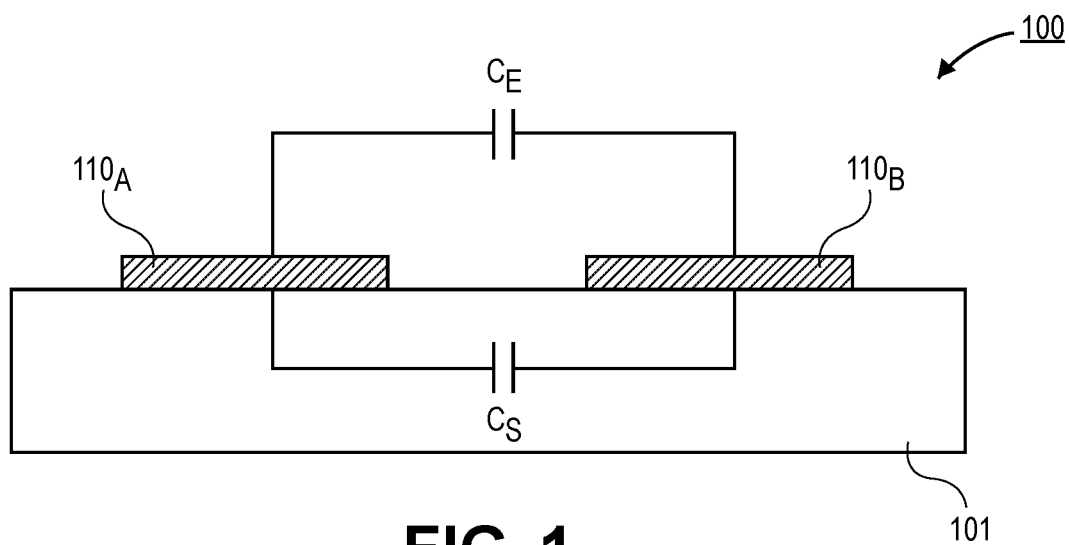
FIG. 1 is a cross-sectional illustration of a capacitive sensor, in accordance with an embodiment.

Referring now to FIG. 1, a cross-sectional illustration of a portion of a capacitive sensor 100 is shown, in accordance with an embodiment. In an embodiment, the capacitive sensor 100 is provided on a substrate 101. The capacitive sensor 100 may comprise a first electrode $110_A$ and a second electrode $110_B$. Capacitances can be read between the first electrode $110_A$ and the second electrode $110_B$. A first capacitance $C_S$ is provided through the substrate 101, and a second capacitance $C_E$ is provided external to the substrate 101. The first capacitance $C_S$ is dependent on the composition of the substrate 101 and the temperature of the substrate 101. In contrast, the second capacitance $C_E$ will change depending on the concentrations, pressure, temperature, etc. of the gasses that flow over the first electrode $110_A$ and the second electrode $110_B$.

In an embodiment, the capacitance can be used to measure the gas concentration using Equation 1. $\varepsilon_r$ is the dielectric constant of the gas, N is the gas density (i.e., gas concentration), $\alpha_e$ is the polarizability of gas molecules, and $\varepsilon_0$ is the vacuum permittivity. $\varepsilon_r$ can be derived from the measured capacitance.

$$\varepsilon_r = 1 + N\alpha_e/\varepsilon_0 \qquad \text{Equation 1}$$

Figure 2A:
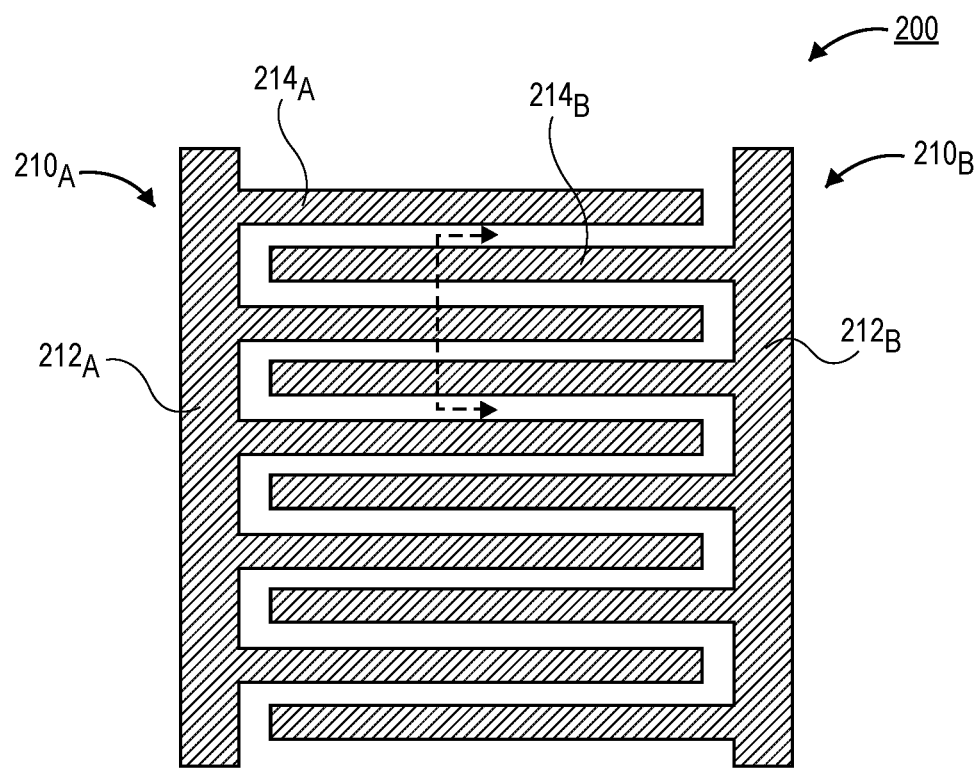
FIG. 2A is a plan view illustration of a capacitive sensor, in accordance with an embodiment.

Referring now to FIG. 2A, a plan view illustration of a sensor 200 is shown, in accordance with an embodiment. The capacitor is made of the first electrode $210_A$ and the second electrode $210_B$ that may have fingers $214_A$ and $214_B$, respectively. The fingers $214_A$ and $214_B$ may extend away from lines $212_A$ and $212_B$, respectively, to scale up the capacitance. In an embodiment, the fingers $214_A$ and $214_B$ are interdigitated as pairs in order to provide an increase in the capacitance between the first electrode $210_A$ and the second electrode $210_B$ by increasing the numbers of electrode pairs. So by scaling the length of fingers 214a and $214_B$ as well as increasing the number of pairs of fingers a proper design can be implemented to achieve high sensitivity.

Figure 2B:
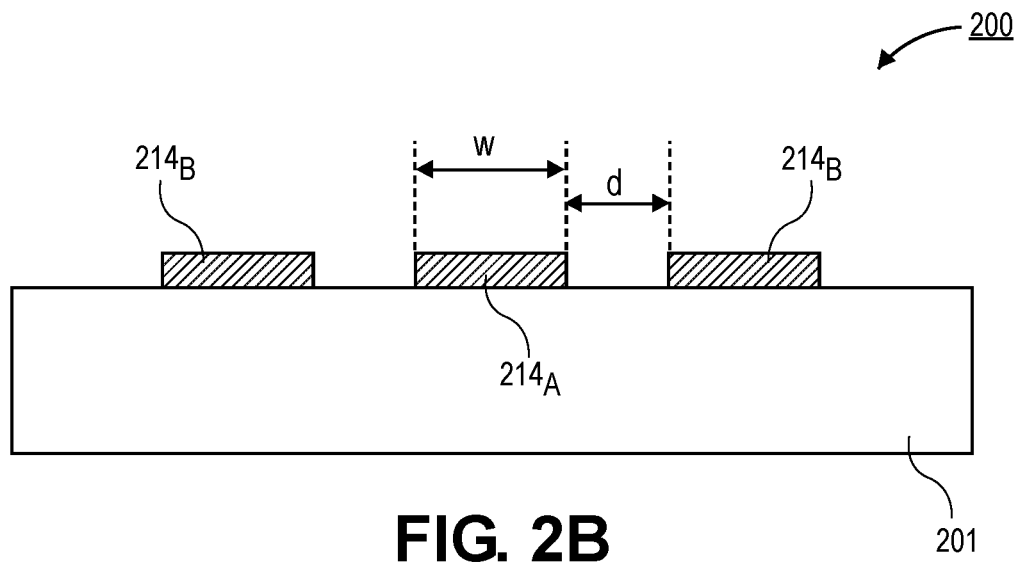
FIG. 2B is a cross-sectional illustration of the capacitive sensor in FIG. 2A, in accordance with an embodiment.

Referring now to FIG. 2B, a cross-sectional illustration of the sensor 200 across the dashed line in FIG. 2A is shown, in accordance with an embodiment. As shown, the fingers $214_A$ and $214_B$ over substrate 201 have a width W and are separated from each other by a distance d. The width W and distance d can be modulated in order to provide good sensitivity.

Figure 3A:
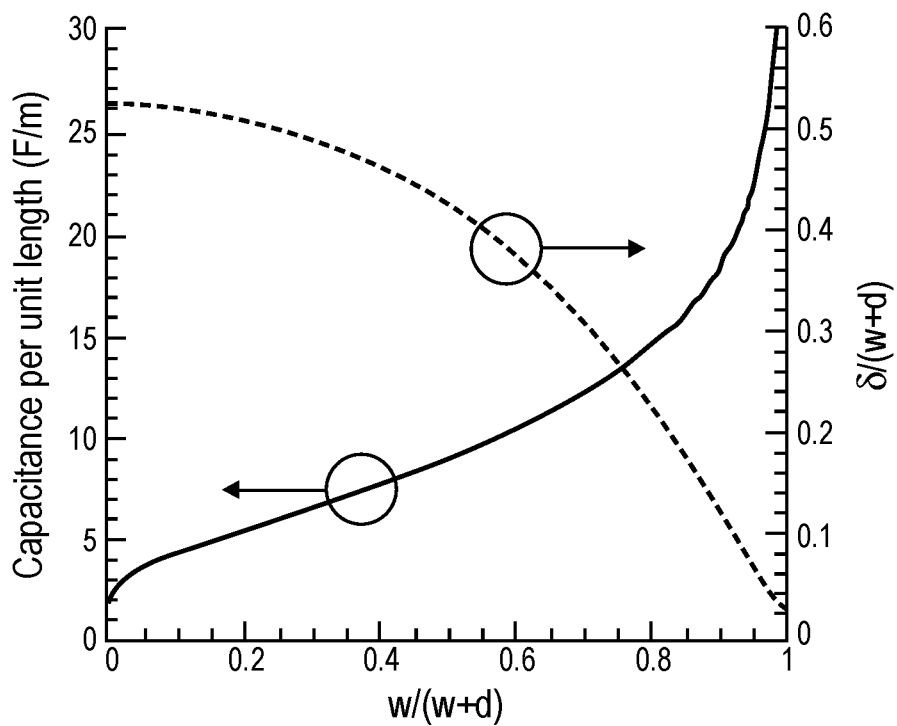
FIG. 3A is a graph of the capacitance per unit length and the field decay length, in accordance with an embodiment.

Referring now to FIG. 3A, a graph of the capacitance per finger per unit length (left side) and the field decay length (right side) is shown, in accordance with an embodiment. As shown, the capacitance depends on the relative dimensions (W/(W+d)). As the distance d is reduced, the capacitance increases and provides more sensitivity to the sensor. However, increases in capacitance result in a decrease in the field, which means the field is confined near the surface area. Having a larger field distribution or penetration allows for more gas above the sensor to be sensed. Accordingly, a balance between field decay length or field penetration to the gas volume and total capacitance may need to be chosen. In a particular embodiment, W/(W+d) may be chosen to be approximately 0.5.

Figure 3B:
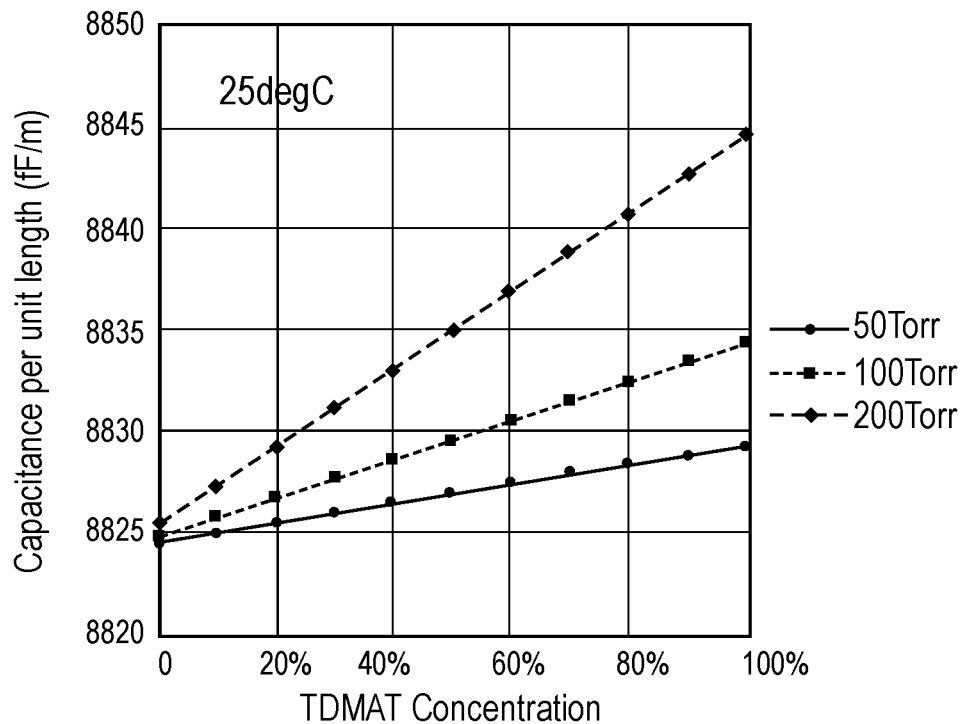
FIG. 3B is a graph illustrating the variance in pressure and the resulting capacitances read by a capacitive sensor, in accordance with an embodiment.
Figure 3C:
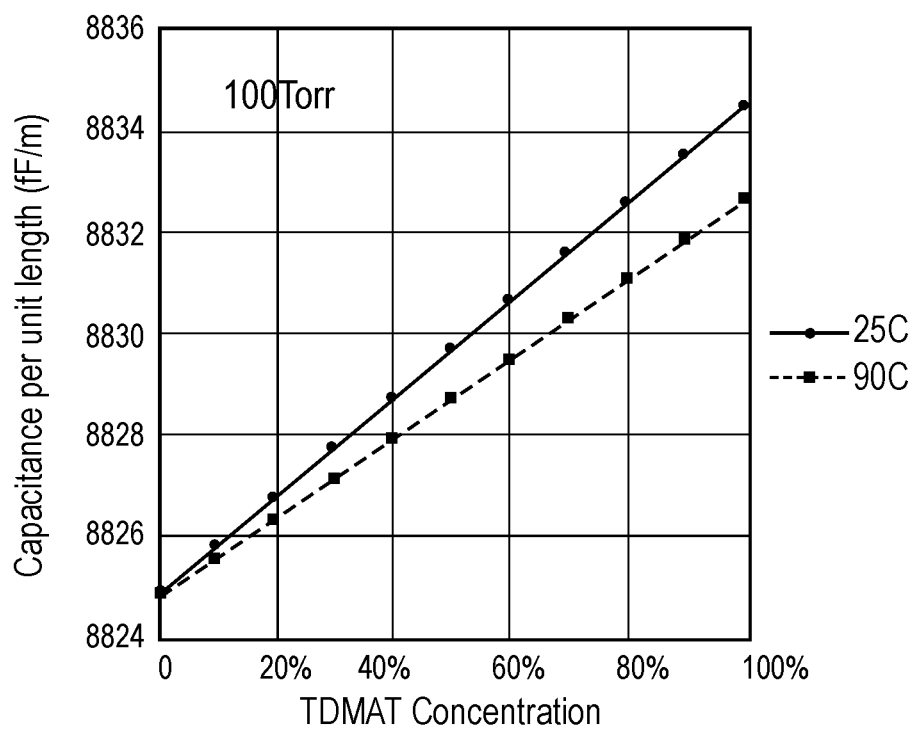
FIG. 3C is a graph illustrating the variance in temperature and the resulting capacitances read by a capacitive sensor, in accordance with an embodiment.

Referring now to FIGS. 3B and 3C graphs depicting capacitance relative to gas concentration for different parameters are shown, in accordance with an embodiment. In FIGS. 3B and 3C, the fingers are assumed to have a W/(W+d) value of 0.5, and the capacitance through the substrate is ignored. The gas concentration of TDMAT in argon between 0% TDMAT and 100% TDMAT is used as an example. As shown in FIG. 3B, increases in the pressure leads to higher capacitances, and as such, higher sensitivities. In some embodiments, a pressure sensor may be coupled with the capacitive gas concentration sensor in order to compensate for pressure variations that may be provided in the readings. As shown in FIG. 3C, lower temperatures lead to increases in capacitance, and as such, higher sensitivities. In some embodiments, a temperature sensor may be coupled with the capacitive gas concentration sensor in order to compensate for thermal noise that may be provided in the readings.

Figure 3D:
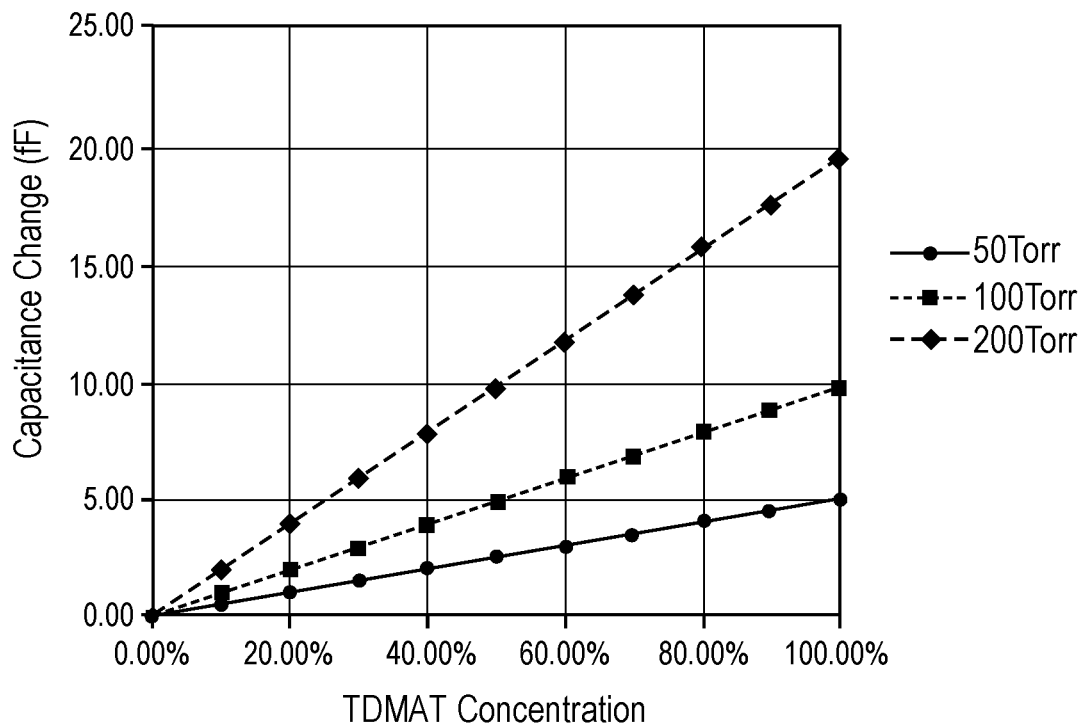
FIG. 3D is a graph illustrating the sensitivity of the capacitor sensor, in accordance with an embodiment.
Figure 3E:
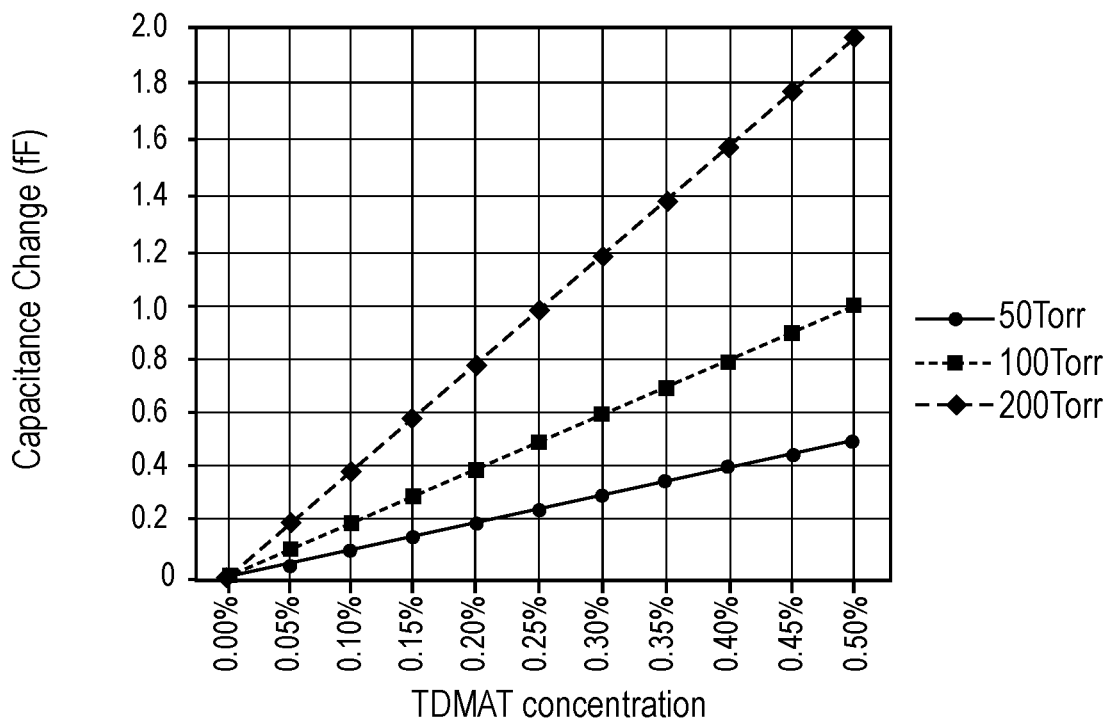
FIG. 3E is a graph illustrating the sensitivity of the capacitor sensor, in accordance with an additional embodiment.

Embodiments disclosed herein allow for high sensitivity. As shown in FIG. 3D, concentration variations down to 1%-3% can be determined depending on the operation pressure. The sensor configuration used to model the sensitivities in FIG. 3D is a W/(W+d) of 0.5, with 1,000 pairs of fingers with a 1 mm finger length, and an overall sensor dimension of 2 mm×10.5 mm. Additional sensitivity can be obtained by scaling up the size of the sensor. For example, with a finger length of 10 mm, 2,000 pairs of fingers, and an overall sensor dimension of 10 mm×10 mm improved sensitivity to be at or less than ppm concentration can be obtained, as shown in FIG. 3E. For example, for the detection of 1% variation over 0.1% relative concentration, it would need the sensitivity of the sensor in the range of 10 ppm.

Figure 4A:
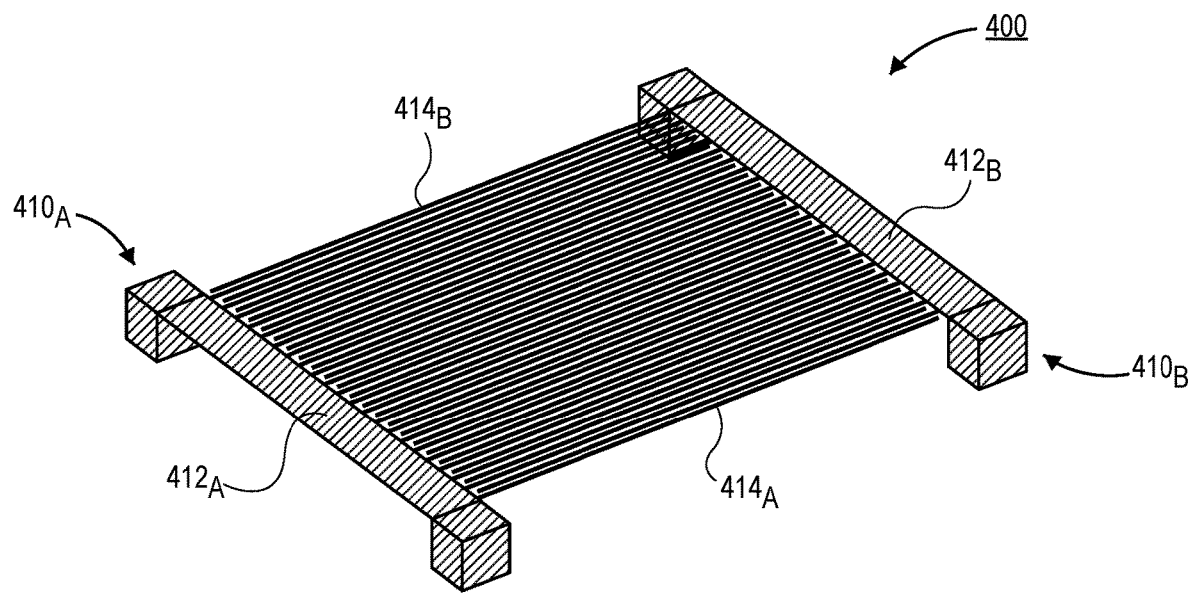
FIG. 4A is a perspective view illustration of a capacitive sensor that is raised up from the substrate by spacers, in accordance with an embodiment.

Referring now to FIG. 4A a perspective view illustration of a capacitive sensor 400 is shown, in accordance with an embodiment. As shown, the capacitive sensor 400 comprises a first electrode $410_A$ and a second electrode $410_B$. In an embodiment, each electrode $410_A$ and $410_B$ may comprise conductive lines $412_A$ and $412_B$ with fingers $414_A$ and $414_B$ extending away from the conductive lines $412_A$ and $412_B$. The fingers $414_A$ may be interdigitated with the fingers $414_B$.

In an embodiment, the conductive lines $412_A$ and $412_B$ may be raised up off or floated from the substrate surface (not shown). By moving the conductive lines $412_A$ and $412_B$ off of the substrate, the gas that is being detected may flow both above and below the fingers 414. As such, the capacitance contributed from the substrate is avoided and a higher portion of the measured capacitance is attributable to the concentration of gasses flowing over the sensor 400. Furthermore the floated electrode designs can minimize the parasitic effects (e.g, thermal noise from the substrates) to improve signal noise ratio (SNR). Higher capacitances can be used to improve the sensitivity of the sensor 400. In a particular embodiment, raising the fingers 414 off of the substrate may allow for a doubling of the sensitivity of the sensor 400. If the sensor 400 was on the substrate, it may be difficult to determine if a change in capacitance was the result of a change in gas concentration or a change in the temperature of the substrate. In an embodiment, the capacitance of the sensor 400 may be determined by applying a DC or AC signal to the fingers 414. However, it is to be appreciated that other signaling regimes may also be used to extract the capacitance value. For example, a spectrum of the sensor with other passive or active elements in the module can be used to extract a resonance frequency signal that may be used to measure the capacitance of the sensor 400 in some embodiments.

Figure 4B:
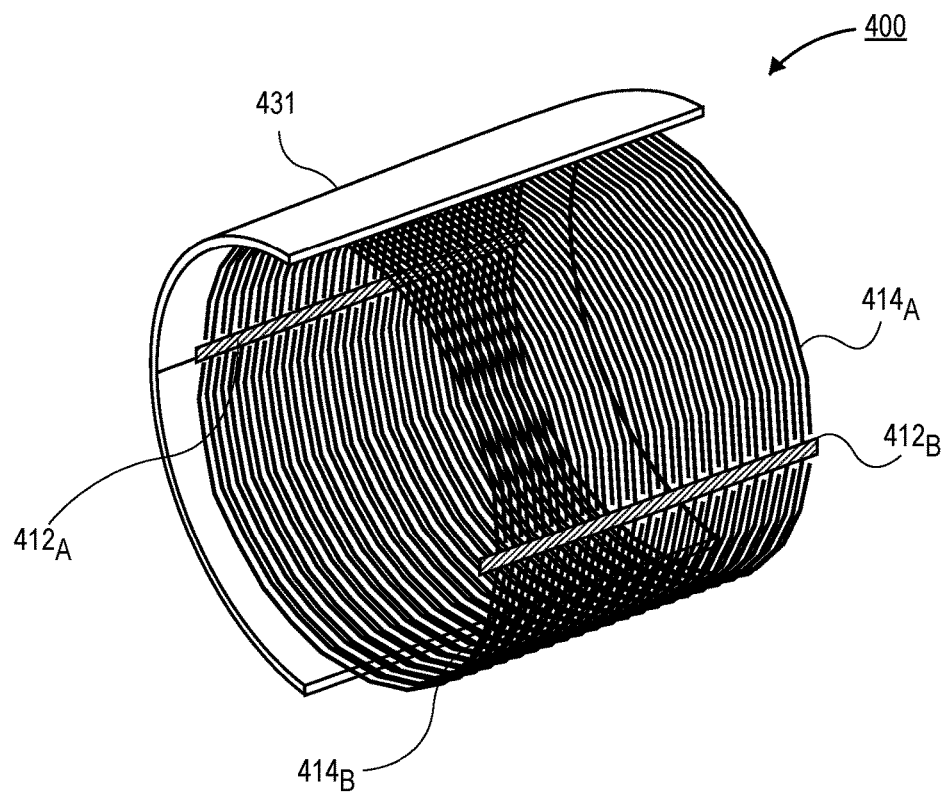
FIG. 4B is a perspective view illustration of a capacitive sensor formed on a flexible substrate that is formed into a shell, in accordance with an embodiment.

Referring now to FIG. 4B, a perspective view illustration of a sensor 400 in accordance with an additional embodiment is shown. In an embodiment, the sensor components may be fabricated on a flexible substrate 431. Since the substrate 431 is flexible, the sensor 400 may be rolled into a tubular shape. This is particularly beneficial for gas concentration sensing, because the sensor 400 can be easily inserted into a gas line. That is, the sensor 400 may be disposed along the interior surface of a gas line. Another implementation will be that all electrodes are conformal to the inner surface of gas line tube but are floated from the surface for better sensitivity. In addition, the sensor electrodes can be directly fabricated on the inner surface of a solid circular tube that is matched to the gas line.

In an embodiment, the sensor 400 may comprise a first line $412_A$ and a second line $412_B$. The first line $412_A$ and the second line $412_B$ may be formed on opposite sides for the tubular sensor 400. In an embodiment, first fingers $414_A$ may extend away from two different surfaces of the first line $412_A$. For example, first fingers $414_A$ may extend upwards and downwards from the first line $412_A$. Similarly, second fingers $414_B$ may extend away from two different surfaces of the second line $412_B$. For example, second fingers $414_B$ may extend upwards and downwards from the second line $412_B$. In an embodiment, the first fingers $414_A$ and the second fingers $414_B$ may be interdigitated with each other.

In some embodiments, the first line $412_A$, the second line $412_B$, the first fingers $414_A$, and the second fingers $414_B$ may be suspended up from the substrate 431 below the first line $412_A$ and the second line $412_B$, similar to the embodiment shown in FIG. 4A. In such instances the gas may be flown over and below the capacitive structures. As such, improved sensitivity is provided. Additionally, complications due to detecting a capacitance through the substrate 431 are avoided.

In an embodiment, providing a tubular sensor 400 also allows for simple scaling of the sensor to improve the sensitivity. Particularly, more fingers $414_A$ and $414_B$ may be provided by extending the length (in the direction of the gas line) of the sensor 400. The length of the sensor 400 is only limited by the length of the gas line, and allows for significant scaling to provide enhanced sensitivities.

Figure 4C:
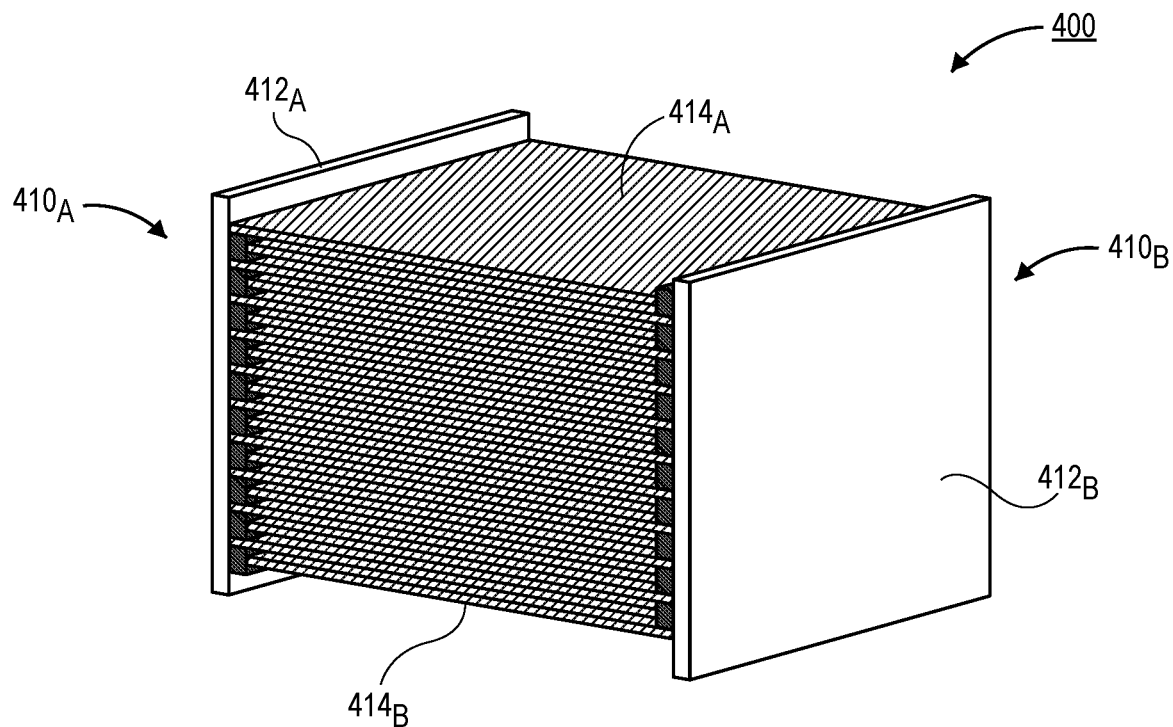
FIG. 4C is a perspective view illustration of a capacitive sensor with plate like fingers that are interdigitated, in accordance with an embodiment.

Referring now to FIG. 4C, a perspective view illustration of a capacitive sensor 400 is shown, in accordance with an embodiment. In an embodiment, the capacitive sensor 400 comprises a first electrode $410_A$ and a second electrode $410_B$. In an embodiment, the first electrode $410_A$ and the second electrode $410_B$ may each comprise a plate $412_A$ and $412_B$. In an embodiment, first fingers $414_A$ may extend out from the first plate $412_A$, and second fingers $414_B$ may extend out from the second plate $412_B$. The first fingers $414_A$ and the second fingers $414_B$ may be plate like features. That is, the first fingers $414_A$ and the second fingers $414_B$ may have lengths and widths that are significantly larger than thicknesses of the first fingers $414_A$ and the second fingers $414_B$.

In an embodiment, the first fingers $414_A$ and the second fingers $414_B$ may be interdigitated with each other. In an embodiment, the first fingers $414_A$ may extend out substantially perpendicular from the first plate $412_A$, and the second fingers $414_B$ may extend out substantially perpendicular from the second plate $412_B$.

Figure 4D:
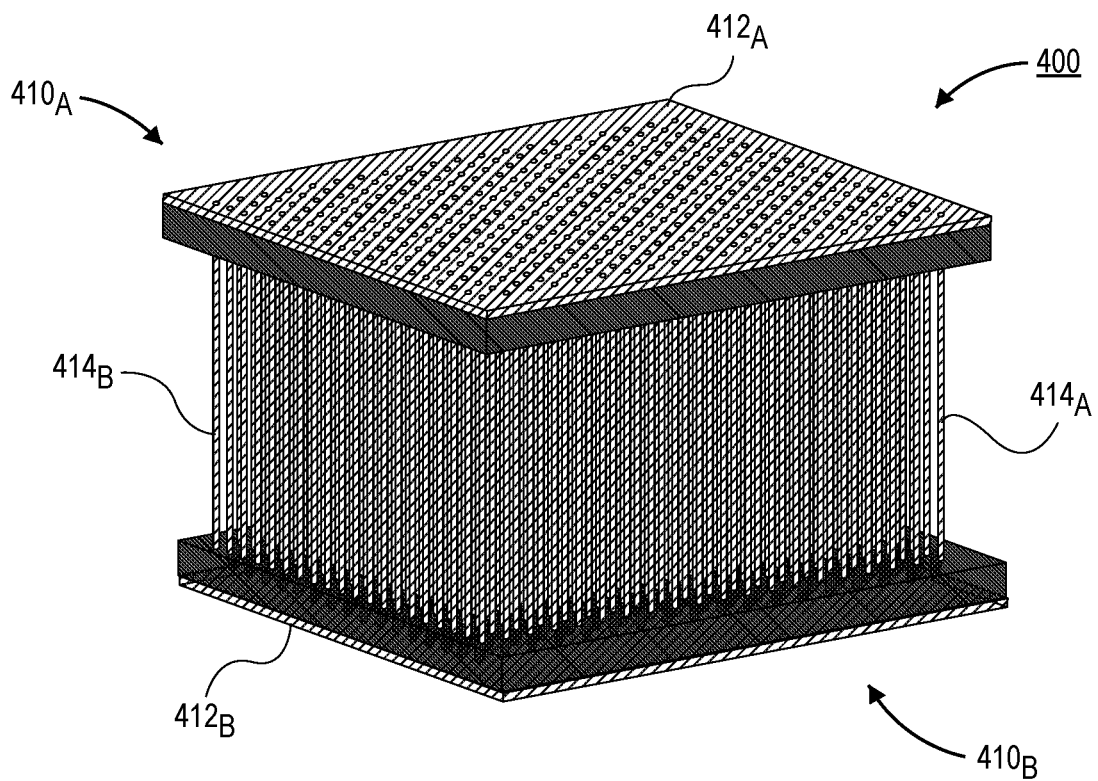
FIG. 4D is a perspective view illustration of a capacitive sensor with pin like fingers that are interdigitated, in accordance with an embodiment.

Referring now to FIG. 4D, a perspective view illustration of a sensor 400 is shown, in accordance with an embodiment. In an embodiment, the sensor 400 may comprise a first electrode $410_A$ and a second electrode $410_B$. The first electrode $410_A$ may comprise a first plate $412_A$ and a plurality of first pins $414_A$. Similarly, the second electrode $410_B$ may comprise a second plate $412_B$ and a plurality of second pins $414_B$. The first pins $414_A$ and the second pins $414_B$ may be disposed in an alternating pattern so that first pins $414_A$ are adjacent to second pins $414_B$. In an embodiment, the pins $414_A$ and $414_B$ may extend out in substantially perpendicular directions from the first plate $414_A$ and the second plate $414_B$.

In addition to different sensor architectures such as those shown in FIGS. 4A-4D, the sensitivity of the sensors may be enhanced through various gas feed architectures. Examples of various gas feed architectures are shown in FIGS. 5A and 5B.

Figure 5A:
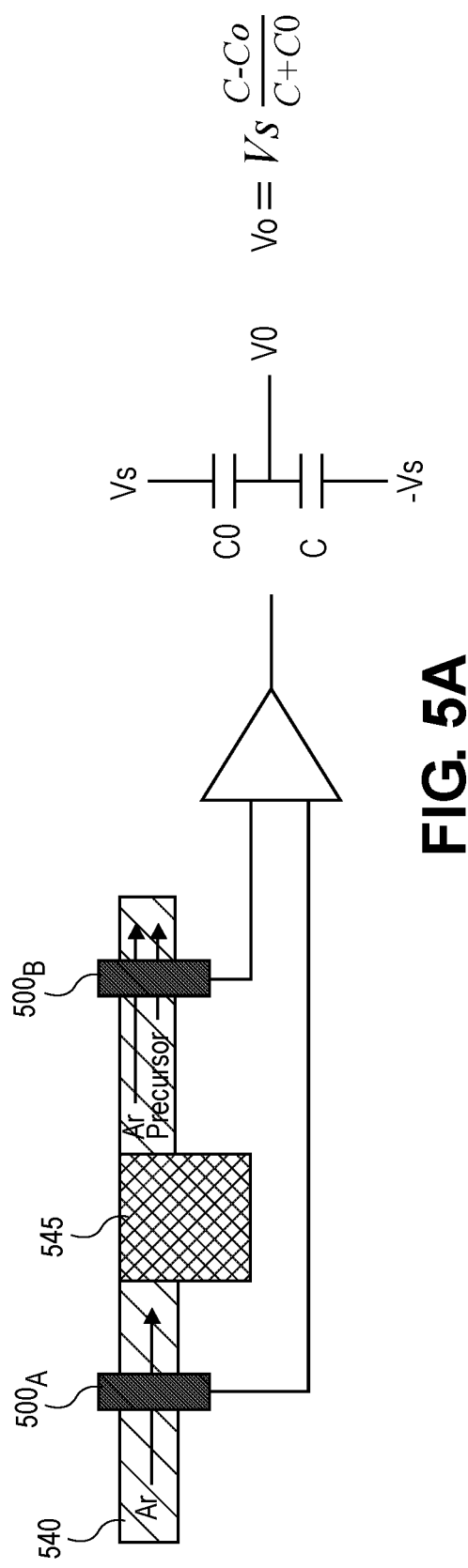
FIG. 5A is a schematic of a gas feed architecture with a pair of capacitive sensors for measuring gas concentration, in accordance with an embodiment.

Referring now to FIG. 5A, a schematic of a gas feed architectures is shown, in accordance with an embodiment. The gas feed architecture may comprise a gas line 540. A first end of the gas line 540 may be connected to a gas source for providing an inert carrier gas, such as argon. An ampule 545 may be provided along the gas line 540. The ampule 545 may provide a second gas to the gas line 540. For example, the second gas may be a precursor, such as TDMAT.

In an embodiment, the gas feed architecture may comprise a pair of gas concentration sensors $500_A$ and $500_B$. The first gas concentration sensor $500_A$ may be before the ampule 545 and the second gas concentration sensor 500 may be after the ampule 545. As shown, readings from the pair of gas concentrations sensors $500_A$ and $500_B$ result in the equivalent circuit shown to the right of the gas feed architecture. A mathematical equation equivalent to the equivalent circuit is $V_O=V_S((C-C_0)/(C+C_0))$. As such, the differential capacitance between $C-C_0$ directly measures the gas concentration from the ampule. In addition, increases to the $V_S$ voltage can be used to increase the measured output $V_O$. That is, increases to $V_S$ can be used to increase the output signal dynamic range of the differential capacitive sensors $500_A$ and $500_B$ to improve signal noise ratio (SNR). In addition, the differential configuration can suppress the common mode noise from thermal, pressure, mechanical drifting noises etc.

Figure 5B:
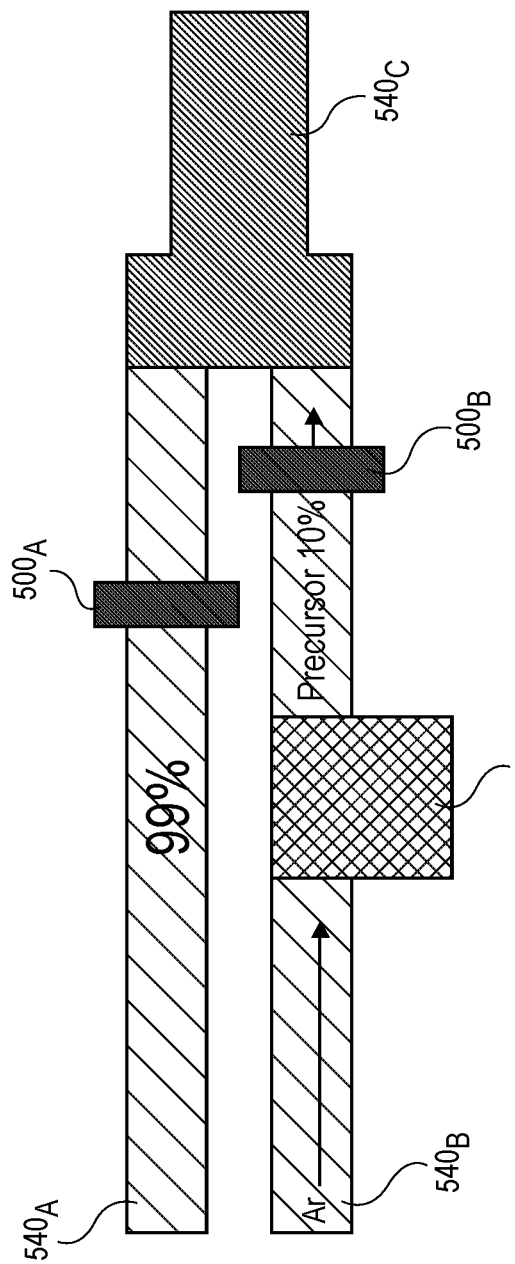
FIG. 5B is a schematic of a gas feed architecture with a first gas line, a second gas line, and a third gas line, and capacitive sensors in the first gas line and the second gas line, in accordance with an embodiment.

Referring now to FIG. 5B, a schematic of a gas feed architecture is shown, in accordance with an additional embodiment. In an embodiment, the gas feed architecture comprises a first gas line $540_A$ and a second gas line $540_B$. The first gas line $540_A$ and the second gas line $540_B$ may merge at a third gas line $540_C$. In an embodiment, the first gas line $540_A$ may supply a first portion of the gas into the third gas line $540_C$ and the second gas line $540_B$ may supply a second portion of the gas into the third gas line $540_C$. For example, the first gas line $540_A$ may supply approximately 90% or more of the gas fed into the third gas line $540_C$, and the second gas line $540_B$ may supply approximately 10% or less of the gas fed into the third gas line $540_C$. In a particular embodiment, the first gas line $540_A$ may supply approximately 99% of the gas into the third gas line $540_C$, and the second gas line $540_B$ may supply approximately 1% of the gas into the third gas line $540_C$.

In an embodiment, the first gas line $540_A$ may supply a first gas, such as an inert gas (e.g., argon), and the second gas line $540_B$ may supply a mixture of the first gas and a second gas, such as a precursor. For example, an ampule 545 along the second gas line $540_B$ may supply the second gas. Since the mixture in the second gas line $540_B$ will subsequently be diluted by the first gas in the first gas line $540_A$, the percentage of the second gas in the second gas line $540_B$ may be relatively large. For example, the second gas may account for approximately 10% of the gas mixture in the second gas line. The larger concentration of the second gas makes it easier to accurately measure the concentrations with the sensor $500_B$. For example, in an embodiment with a 99% gas flow in the first gas line $540_A$ and a 10% concentration of the second gas in the second gas line $540_B$, the final concentration in the third gas line $540_C$ is approximately 0.1%. As such, embodiments disclosed herein only need to be able to measure a gas concentration that is two orders of magnitude larger than the targeted gas concentration.

As noted above, the capacitance readings of the sensors may also be impacted by temperature and pressure changes. Accordingly, some embodiments may include sensors that further comprise a temperature sensor and/or a pressure sensor. Therefore, embodiments allow for changes in temperature and pressure to be monitored for by the sensor. With the proper sensing algorithm, thermal and pressure parasitic effects can be compensated by directly monitoring the temperature and pressure of gases to improve the monitoring accuracy as well as sensitivity of gas concentration. Examples of such sensors are provided in FIGS. 6A and 6B.

Figure 6A:
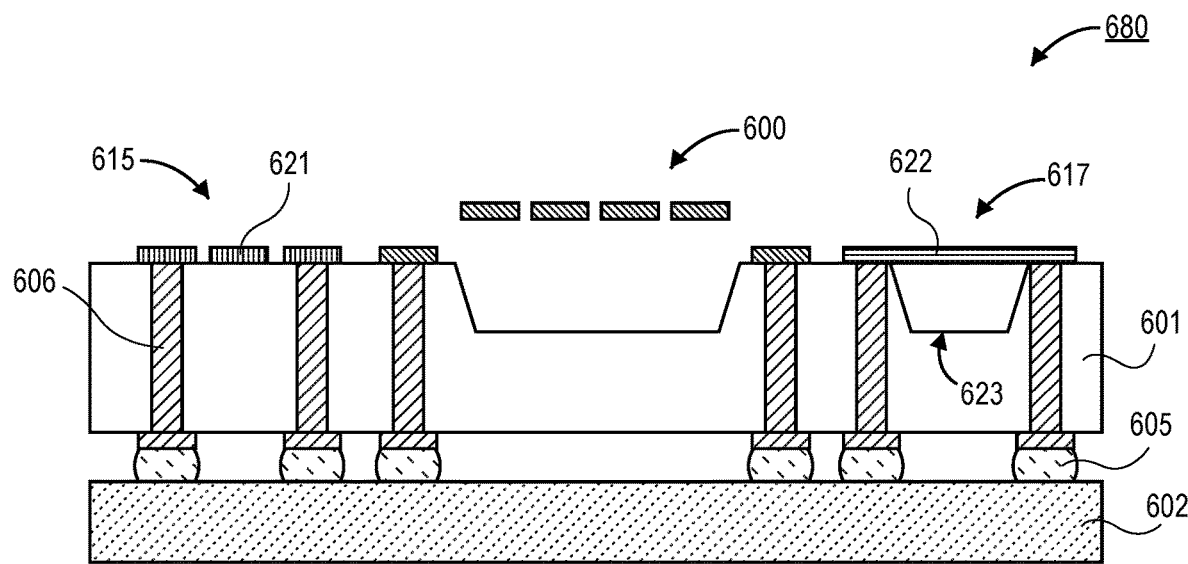
FIG. 6A is a cross-sectional illustration of a sensor system with a gas concentration sensor, a temperature sensor, and a pressure sensor that are integrated on one substrate or module with a processor, in accordance with an embodiment.

Referring now to FIG. 6A, a cross-sectional illustration of a sensor system 680 is shown, in accordance with an embodiment. In an embodiment, the sensor system 680 comprises a sensor substrate 601. The sensor substrate 601 may be electrically and mechanically coupled to a processor 602, such as an ASIC or the like. For example, solder balls 605 may be used to connect the sensor substrate 601 to the processor 602.

The sensor system 680 may comprise a capacitive sensor 600, a temperature sensor 615, and a pressure sensor 617. The sensors 600, 615, and 617 may be electrically coupled to the solder balls 605 by through substrate vias 606. In an embodiment, the capacitive sensor 600 may be substantially similar to any of the capacitive sensors for gas compensation detection described in greater detail above. In an embodiment, the temperature sensor 615 may be a resistance temperature detector (RTD). For example, changes in a resistance across a conductive trace 621 may be used to measure the change in temperature. Other thermal sensors can also be integrated such as semiconductor junction sensor, acoustic wave sensor, and thermistor, etc. The typical temperature sensing resolution can be 0.01 degree to 0.1 degree. The temperature range may be from room temperature to 650 C. In an embodiment, the pressure sensor 617 may comprise a piezoelectric or capacitive sensor. For example, a diaphragm 622 may span across a trench 623 in the sensor substrate 601. The sensitivity for the pressure sensor can range from a few millitorr (e.g., 10 mT) to 1 torr with the pressure range from 10 Torr to 760 Torr. It is to be appreciated that temperature sensors 615 and pressure sensors 617 similar to those shown in FIG. 6A may be fabricated on the sensor substrate 601 using standard semiconductor manufacturing processes. As such, integration of such sensors can be implemented at a substantially low cost. However, it is to be appreciated that one or both of the temperature sensor 615 and the pressure sensor 617 may be provided as discrete components that are attached to the sensor substrate 601.

Figure 6B:
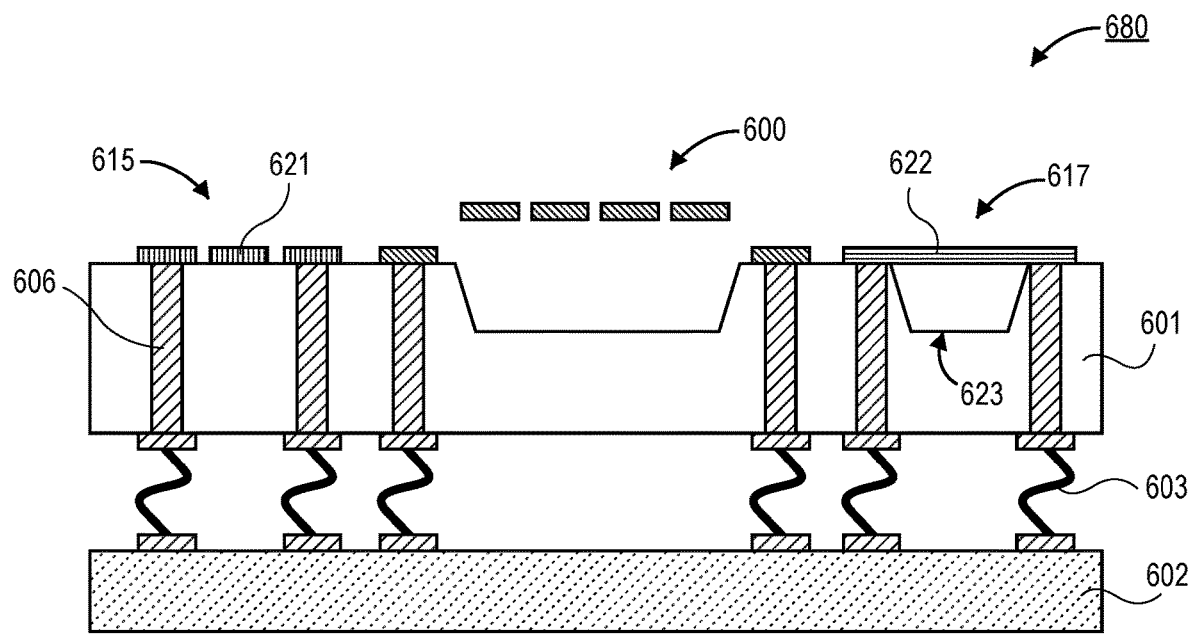
FIG. 6B is a cross-sectional illustration of a sensor system with a gas concentration sensor, a temperature sensor, and a pressure sensor that are coupled to a processor by an interconnect, in accordance with an embodiment.

Referring now to FIG. 6B, a cross-sectional illustration of a sensor system 680 is shown, in accordance with an additional embodiment. The sensor system 680 may be substantially similar to the sensor system 680 in FIG. 6A, with the exception of the interconnect between the sensor substrate 601 and the processor 602. Instead of attaching the processor 602 to the sensor substrate 601 by solder balls, interconnects such as wire bonds 603 are used. The use of wire bonds 603 allows for the processor 602 to be remote from the sensor substrate 601. For example, the sensor substrate 601 may be provided within a gas line and the processor 602 may be external to the gas line. Such embodiments are particularly useful when the processing conditions (e.g., temperature) exceed the operating range of the processor 602. For example, the safe operating maximum of the processor 602 may be approximately 150° C., and the gas processing temperature may be above 150° C. As such, the operating range of the sensor system 680 may be increased by removing the processor 602 from the processing environment.

Figure 7:
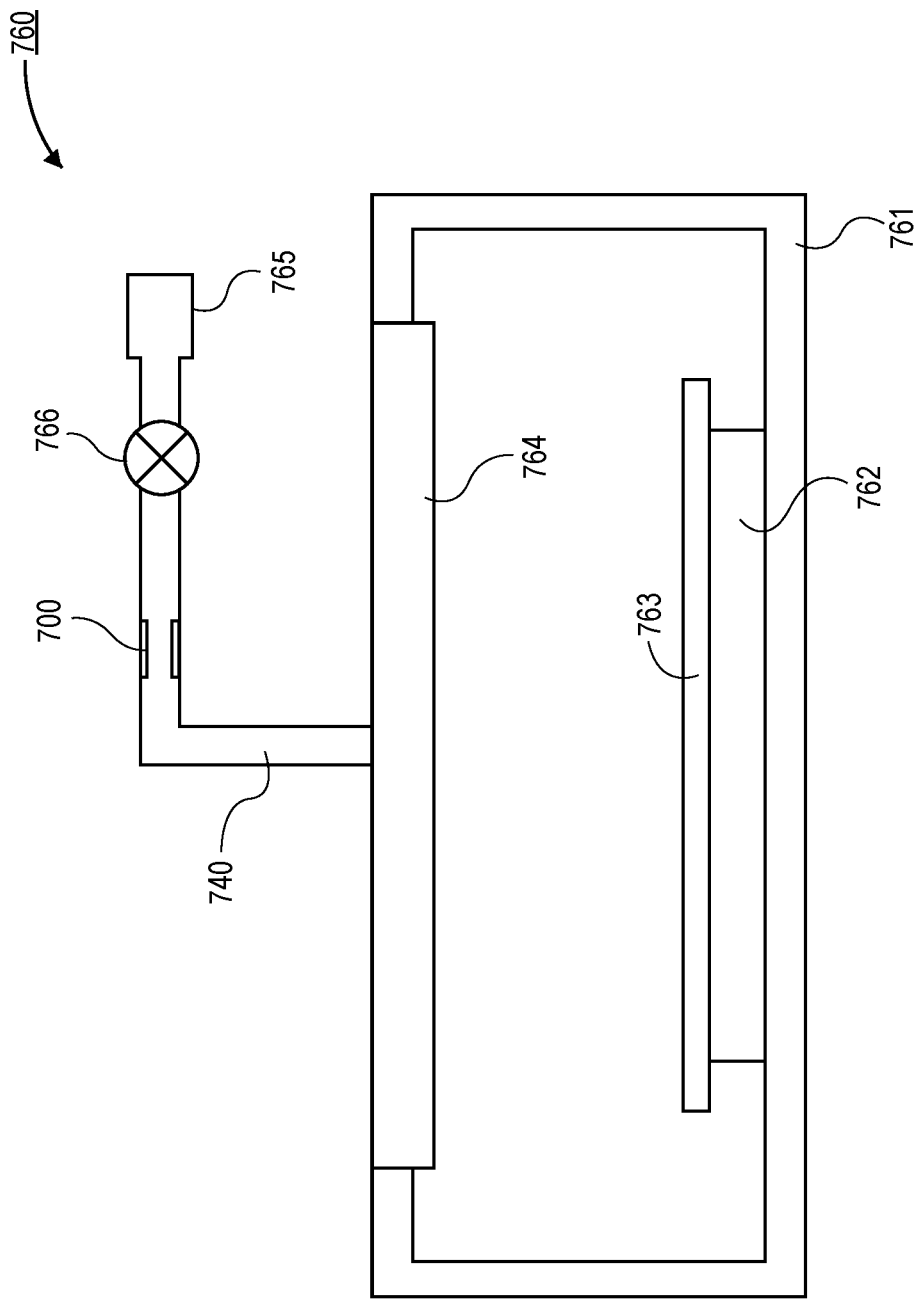
FIG. 7 is a cross-sectional illustration of a semiconductor processing tool with a capacitive gas concentration sensor, in accordance with an embodiment.

Referring now to FIG. 7, a cross-sectional illustration of a semiconductor processing tool 760 is shown, in accordance with an embodiment. In an embodiment, the semiconductor processing tool 760 is a tool that includes the flow of one or more processing gasses 765 into a chamber 761. For example, the semiconductor processing tool may comprise an atomic layer deposition (ALD) tool, a chemical vapor deposition (CVD) tool, a physical vapor deposition (PVD) tool, an etching tool, or any other semiconductor processing tool that includes the flow of gas or gasses into the chamber 761.

The chamber 761 may be suitable for providing sub-atmospheric pressures in order to process one or more substrates 763. For example, a vacuum pump (not shown) may be fluidically coupled to the chamber 761. In an embodiment, the substrate 763 may be supported on a pedestal 762 or the like. The pedestal 762 may comprise a chucking mechanism (e.g., electrostatic chucking, vacuum chucking, etc.). The pedestal 762 may also comprise heating and/or cooling functionality to control a temperature of the substrate 763.

In an embodiment, gas from a gas source 765 may flow into a gas line 740 by passing through a valve 766. The gas source 765 may hold the substance in a gas phase or a liquid phase. In an embodiment, a gas concentration sensor 700 may be integrated into the gas line 740. The gas concentration sensor 700 may be similar to any of the gas concentration sensors described in greater detail above. Particularly, in an embodiment, the gas concentration sensor 700 comprises a first electrode and a second electrode with interdigitated fingers to provide a high capacitance value. Changes to the capacitance can be used to determine the concentration of the gasses flowing through the gas line 740. The gas line 740 may feed into a showerhead 764 for distributing the gasses into the chamber 761. In an embodiment, the showerhead 764 may also be suitable for generating a plasma in the chamber to enable plasma assisted processing operations (e.g., PE-ALD, PE-CVD, etc.).

In addition to measuring a gas concentration of a gas flowing into the chamber 761, embodiments may include placing the gas concentration sensor 700 in various other locations of the processing tool 760. For example, the gas concentration sensor 700 may be used for detecting when a cleaning operation is completed. In such an embodiment, the gas concentration sensor 700 may be placed inside process chamber near the vacuum port or in the exhaust line. The gas concentration sensor 700 may be used to determine certain gas molecules or species in byproducts during the cleaning, for example, when carbon is no longer present in the byproducts. When the concentration of carbon goes below a given threshold, it can be determined that the cleaning of the chamber is completed.

In yet another embodiment, the gas concentration sensor 700 may be used for chamber condition monitoring. For example, a gas concentration sensor 700 within the chamber 761 may be able to detect gas concentrations that can be monitored for chamber health. Additionally, the gas concentration sensor 700 may be used to monitor de-absorption of chemical species from the walls of the chamber 761. In yet another embodiment, the gas concentration sensor 700 may be integrated into an abatement system in order to monitor the disposal of processing gasses and byproducts from the processing tool 760.

Embodiments also include the use of a gas concentration sensor 700 in doping processes such as ion implantation. For example, a concentration of the dopant gas can be determined in order to more accurately determine a dopant concentration that will result on the substrate. As such, improved control of doping processes are enabled.

Figure 8:
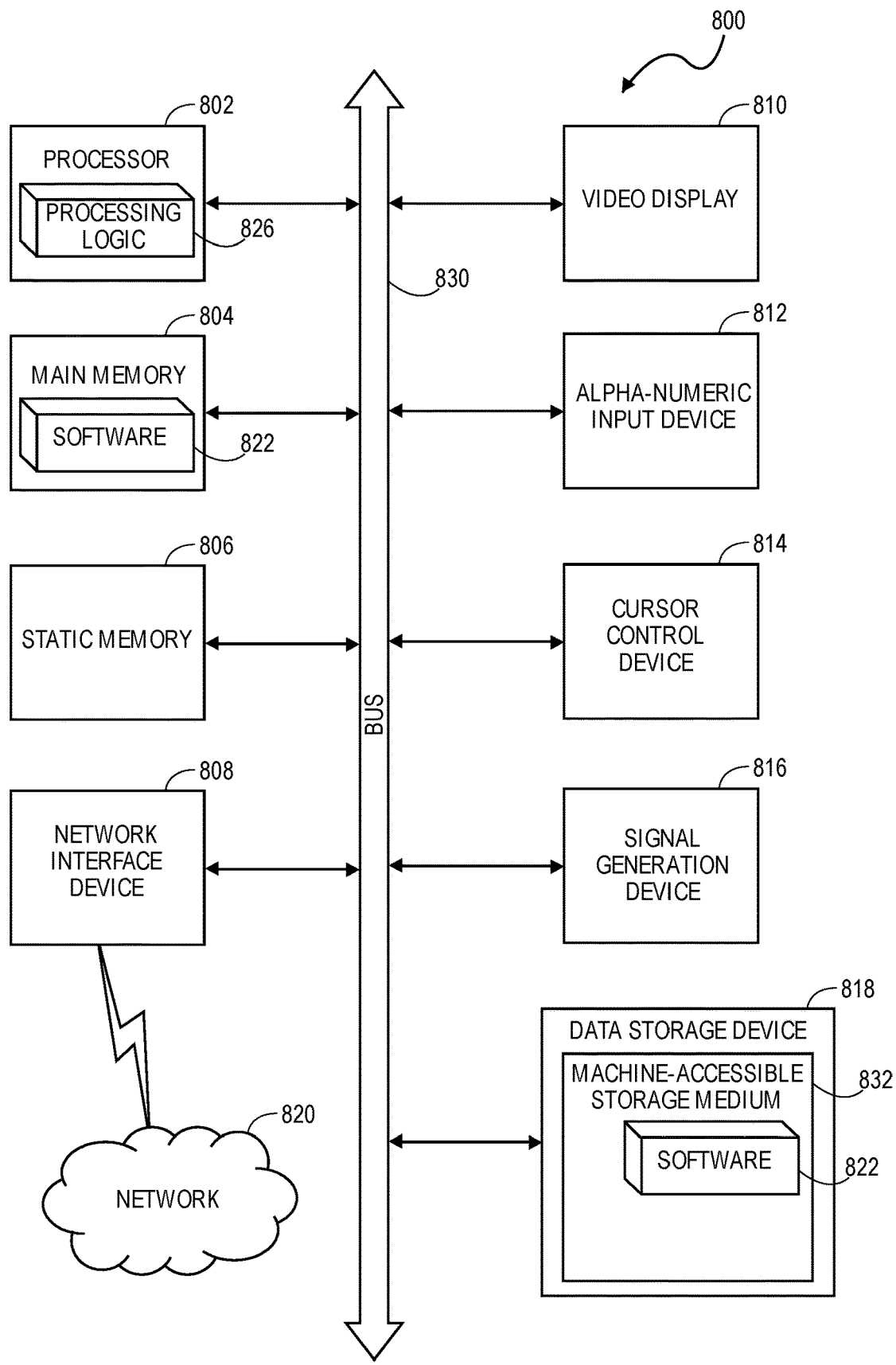
FIG. 8 illustrates a block diagram of an exemplary computer system, in accordance with an embodiment of the present disclosure.

FIG. 8 illustrates a diagrammatic representation of a machine in the exemplary form of a computer system 800 within which a set of instructions, for causing the machine to perform any one or more of the methodologies described herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies described herein.

The exemplary computer system 800 includes a processor 802, a main memory 804 (e.g., read-only memory (ROM), flash memory, dynamic random access memory (DRAM) such as synchronous DRAM (SDRAM) or Rambus DRAM (RDRAM), etc.), a static memory 806 (e.g., flash memory, static random access memory (SRAM), MRAM, etc.), and a secondary memory 818 (e.g., a data storage device), which communicate with each other via a bus 830.

Processor 802 represents one or more general-purpose processing devices such as a microprocessor, central processing unit, or the like. More particularly, the processor 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 802 may also be one or more special-purpose processing devices such as an application specific integrated circuit (ASIC), a field programmable gate array (FPGA), a digital signal processor (DSP), network processor, or the like. Processor 802 is configured to execute the processing logic 826 for performing the operations described herein.

The computer system 800 may further include a network interface device 808. The computer system 800 also may include a video display unit 810 (e.g., a liquid crystal display (LCD), a light emitting diode display (LED), or a cathode ray tube (CRT)), an alphanumeric input device 812 (e.g., a keyboard), a cursor control device 814 (e.g., a mouse), and a signal generation device 816 (e.g., a speaker).

The secondary memory 818 may include a machine-accessible storage medium (or more specifically a computer-readable storage medium) 832 on which is stored one or more sets of instructions (e.g., software 822) embodying any one or more of the methodologies or functions described herein. The software 822 may also reside, completely or at least partially, within the main memory 804 and/or within the processor 802 during execution thereof by the computer system 800, the main memory 804 and the processor 802 also constituting machine-readable storage media. The software 822 may further be transmitted or received over a network 820 via the network interface device 808.

While the machine-accessible storage medium 832 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, and optical and magnetic media.

In accordance with an embodiment of the present disclosure, a machine-accessible storage medium has instructions stored thereon which cause a data processing system to perform a method of measuring the gas concentration of a gas flown in a gas line using a capacitive gas concentration sensor.

Thus, methods for measuring gas concentration have been disclosed.

What is claimed is:

1. A semiconductor processing tool, comprising: a chamber; a gas line for providing a source gas to the chamber; and a gas concentration sensor in the gas line, wherein the gas concentration sensor comprises: a first electrode, wherein the first electrode comprises first fingers; and a second electrode, wherein the second electrode comprises second fingers that are interdigitated with the first fingers, the first electrode comprising a first plate along a vertical direction relative to the substrate, the second electrode comprising a second plate along the vertical direction, and the first fingers and second fingers laterally between the first electrode and the second electrode along a horizontal direction relative to the substrate, and wherein the second electrode is capacitively coupled to the first electrode to provide a capacitance to measure a gas concentration.

2. The semiconductor processing tool of claim 1, wherein the first fingers and the second fingers are plates or pins.

3. The semiconductor processing tool of claim 1, wherein gas flows through the interdigitated first fingers and second fingers.

4. The semiconductor processing tool of claim 1, wherein the semiconductor processing tool is an atomic layer deposition (ALD) tool.

5. A gas feed architecture, comprising: a first gas line, wherein the first gas line receives a first gas from a first gas source; an ampule along the first gas line, wherein the ampule supplies a second gas to the first gas line; a first gas concentration sensor after the ampule, wherein the first gas concentration sensor comprises: a first electrode, wherein the first electrode comprises first fingers;

and a second electrode, wherein the second electrode comprises second fingers that are interdigitated with the first fingers, the first electrode comprising a first plate along a vertical direction relative to the substrate, the second electrode comprising a second plate along the vertical direction, and the first fingers and second fingers laterally between the first electrode and the second electrode along a horizontal direction relative to the substrate, and wherein the second electrode is capacitively coupled to the first electrode to provide a capacitance to measure a gas concentration.

6. The gas feed architecture of claim 5, further comprising:
a second gas sensor before the ampule.

7. The gas feed architecture of claim 5, further comprising:
a second gas line, wherein the second gas line receives the first gas, and wherein the second gas line merges with the first gas line at a third gas line.

8. The gas feed architecture of claim 7, wherein the first gas concentration sensor is between the ampule and the third gas line.

9. The gas feed architecture of claim 7, further comprising:
a second gas sensor on the second gas line.

10. The gas feed architecture of claim 9, wherein approximately 90% or more of gas flow into the third gas line is from the second gas line, or wherein approximately 1% or less of gas flow into the third gas line is the second gas.

11. A semiconductor processing tool, comprising:
a chamber; and
a gas concentration sensor coupled to the chamber, wherein the gas concentration sensor comprises:
a first electrode above a substrate, wherein the first electrode comprises first fingers; and
a second electrode above the substrate, wherein the second electrode comprises second fingers that are interdigitated with the first fingers, the first electrode comprising a first plate along a vertical direction relative to the substrate, the second electrode comprising a second plate along the vertical direction, and the first fingers and second fingers laterally between the first electrode and the second electrode along a horizontal direction relative to the substrate, and wherein the second electrode is capacitively coupled to the first electrode to provide a capacitance to measure a gas concentration.

12. The semiconductor processing tool of claim 11, wherein the first electrode and the second electrode of the gas concentration sensor are raised up from a surface of the substrate.

13. The semiconductor processing tool of claim 11, wherein the substrate of the gas concentration sensor is a flexible substrate.

14. The semiconductor processing tool of claim 13, wherein the flexible substrate of the gas concentration sensor is cylindrical.

15. The semiconductor processing tool of claim 13, wherein the first electrode of the gas concentration sensor comprises a first line, wherein the first fingers extend away from the first line from two surfaces of the first line, and wherein the second electrode of the gas concentration sensor comprises a second line, wherein the second fingers extend away from the second line from two surfaces of the second line.

16. The semiconductor processing tool of claim 11, wherein the first fingers and the second fingers of the gas concentration sensor are plates.

17. The semiconductor processing tool of claim 11, wherein the first fingers and the second fingers of the gas concentration sensor are pins.

18. The semiconductor processing tool of claim 11, wherein the gas concentration sensor is provided in a gas feed line of the semiconductor processing tool.

19. The semiconductor processing tool of claim 11, wherein the gas concentration sensor further comprises:
a temperature sensor; and
a pressure sensor.

* * * * *